United States Patent [19]
LaPack et al.

[11] Patent Number: 5,354,474
[45] Date of Patent: Oct. 11, 1994

[54] DYNAMIC MEMBRANE SEPARATION PROCESS FOR IMPROVED SELECTIVITY

[75] Inventors: Mark A. LaPack, Midland, Mich.; P. Foppe Dupuis, Axel, Netherlands

[73] Assignee: The Dow Chemical Company, Midland, Mich.

[21] Appl. No.: 8,104

[22] Filed: Jan. 25, 1993

Related U.S. Application Data

[63] Continuation-in-part of Ser. No. 772,619, Oct. 8, 1991, abandoned, which is a continuation of Ser. No. 455,471, Dec. 22, 1989, abandoned, which is a continu-

[51] Int. Cl.$^5$ ............................................. B01D 65/08
[52] U.S. Cl. ................................... 210/637; 210/640; 210/651; 210/652
[58] Field of Search ............... 210/86, 240, 640, 651, 210/652, 639, 641, 637; 55/16, 74, 68, 158

[56] References Cited

U.S. PATENT DOCUMENTS

| | | | |
|---|---|---|---|
| 3,757,947 | 9/1973 | Wakefield et al. | 210/95 X |
| 3,796,314 | 3/1974 | Kolek | 210/321 |
| 3,818,679 | 6/1974 | Klass et al. | 55/16 |
| 3,969,240 | 7/1976 | Kolobow et al. | 210/22 A |
| 4,077,885 | 3/1978 | van Heuven et al. | 210/193 |
| 4,093,515 | 6/1978 | Kolobow | 195/1.8 |
| 4,349,356 | 9/1982 | Wakao | 55/16 |
| 4,664,683 | 5/1987 | Degen et al. | 55/387 |
| 4,665,050 | 5/1987 | Degen et al. | 502/402 |
| 4,765,915 | 8/1988 | Diehl | 210/767 |

*Primary Examiner*—Frank Spear
*Attorney, Agent, or Firm*—Timothy S. Stevens

[57] ABSTRACT

A membrane separation and purification process, and the associated apparatus, provides separation of one membrane-permeable component from another, where both are contained in a multiple-component fluid mixture, as a dynamic function of the differences in respective rates of attainment of and declination from steady-state membrane permeation. The process and apparatus are equally well suited to multi-component fluid mixtures that are liquid or gaseous.

21 Claims, 11 Drawing Sheets

FIG. IIC

FIG. IIB

Fig. 12

DYNAMIC MEMBRANE SEPARATION PROCESS FOR IMPROVED SELECTIVITY

CROSS-REFERENCE TO RELATED APPLICATIONS

This application is a Continuation-in-Part of the co-pending application Ser. No. 07/772,619, filed Oct. 8, 1991., now abandoned, which is a Continuation of application Ser. No. 07/455,471, filed Dec. 22, 1989, now abandoned.

Field of the Invention

The present invention relates to membrane separation apparatus and processes for improved separation selectivity, and more particularly, to apparatus and processes wherein a semi-permeable membrane is used for selective enrichment of either a permeate from a multi-component feed mixture or for purifying the mixture itself.

BACKGROUND

Permeation of one component of a multi-component fluid mixture through a permeable membrane is related to the solubility coefficient, which describes the ability of the membrane to extract that component from the feed mixture, and the diffusion coefficient, which describes how fast that component will transport across the thickness of the membrane. These coefficients are constant for a given compound/membrane system for a given solvent and at constant temperatures.

Permeable membranes are used in a variety of contexts to separate a component of interest from a multi-component feed mixture. For example, in applications where a multi-component feed mixture has a single membrane-permeable component, that component is separated from the feed mixture by exposing the feed mixture to a permeable membrane. Since only the one component is membrane-permeable, that component is separated from the feed mixture and is collected from the other side of the membrane. In a separation process of this type, recovery of the permeating component or she "permeate" (i.e., the fluid which permeates the membrane) in any given time period is maximized by operating the membrane separation process at steady state permeation. Steady state permeation means that the rate of permeation of the permeating component essentially does not change with time. In addition, during steady state permeation the total throughput of the permeating component is maximized.

When a multi-component feed mixture having more than one membrane-permeable component is introduced to a permeable membrane, the resulting permeate will consist of all the membrane-permeable components from the multi-component feed mixture. Under steady state conditions, maximum throughput of the membrane permeable components will be realized and the proportion of each of those components in the permeate will be directly proportional to the rate of steady state permeation of each component. That is, when a multi-component feed which has two membrane-permeable components is introduced to a permeable membrane, two membrane-permeable components are separated from the other components of the feed mixture. The relative proportions of each of those two components in the permeate when the system is operated at steady-state is dependent upon the rate of steady-state permeation of each component.

The known membrane separation processes do not provide relative separation of individual membrane-permeable components vis-a-vis one another apart from the separation which occurs due to the differences in the rates of steady state permeation of the components.

Summary of the Invention

It is oftentimes desirable to provide a greater degree of separation of two or more membrane-permeable components relative to one another than is currently possible using known steady state membrane permeation. This need arises in both chemical analysis and other contexts. For example, in mass spectrometry, it is desirable to minimize the signal of the interferent relative to the analyte. This is possible by maximizing the proportion of the analyte relative to the interferent in the permeate from a permeable membrane. Additionally, in purification processes, it is often the case that two or more components in a multi-component fluid mixture are membrane-permeable and need to be separated from one another. The known membrane separation processes described above do not solve the problem of maximizing the separation of one membrane-permeable component relative another membrane-permeable component in a multi-component fluid mixture.

The present invention is directed to a membrane separation process, and the associated apparatus, which provides separation of one membrane-permeable component from another where both are contained in a multiple-component fluid mixture. The process and apparatus of this invention are equally well suited to multi-component fluid mixtures that are liquid or gaseous.

According to the invention, one embodiment of a membrane separation process is operated under non-steady state or dynamic conditions to provide increased selectivity in separating membrane-permeable components relative one another. The process, by operating under non-steady state conditions, takes advantage of the differential in the rates of attainment of steady-state permeation and the rates of fall-off from steady-state permeation of membrane-permeable compounds. The differentials in the rates of attaining steady-state permeation and fall-off from steady-state permeation by permeating compounds is based in large part upon the differences in the diffusivities of the permeating compounds.

When a feed stream containing two membrane-permeable compounds is exposed to a membrane, the permeation of each compound increases from an initial base line value to its steady-state value. This initial region of a permeation response curve is termed "sorption". "Desorption," which is the sorption process reversed, is where the introduction of the feed to the membrane is discontinued and the permeation response curve falls off from its steady-state value to a base line value. During the sorption process, compounds which have a faster rate of attainment of steady-state permeation, i.e., faster diffusing compounds, are enriched in the permeate over slower diffusing compounds, relative to the enrichment that is possible under steady-state conditions. Likewise, compounds which have a slower rate of attainment of steady-state permeation and therefore a slower rate of fall-off from steady-state permeation, i.e., slower diffusing compounds, are enriched in the permeate over faster diffusing compounds during the desorption process.

Sorption and desorption, by their nature, represent dynamic, non-steady state conditions. For this reason, neither sorption nor desorption can be maintained indefinitely. Thus, for the enhanced separation of membrane-permeable components from a feed stream relative one another, a continuous process requires a discontinuous feed stream.

In a process exploiting sorption, the feed stream is preferably interrupted after sufficient time has elapsed for one or more faster diffusing membrane-permeable components to approach or reach steady state permeation of the membrane, but prior to a slower diffusing compound or compounds reaching steady state permeation of the membrane. The permeate is collected during the period of sorption, and, in this manner, the differential in the rates of attainment of steady state permeation of the membrane-permeable components is exploited to produce a permeate enriched in a faster diffusing compound.

In a process exploiting desorption, the permeate is collected beginning at a time when the feed stream, which is at or near steady-state permeation or at some non-baseline permeation, has been interrupted to thereby exploit the differential in the fall-off rates from steady-state permeation to a base line value of the membrane-permeable compounds. The permeate collected is enriched in the slower diffusing compounds.

In one preferred form of the process of the present invention, a multi-component fluid mixture feed having at least two membrane-permeable components, wherein a first component approaches steady-state permeation of a membrane at a faster rate than a second component, is introduced to a first side of a permeable membrane for a predetermined period of time to selectively separate the first component from the second component. The predetermined time period is preferably less than that required for the second component to reach steady-state permeation of the membrane since that results in the greatest degree of enrichment of the first component. After the predetermined time period has elapsed, the introduction of feed to the first side of the membrane is discontinued or interrupted. The permeate enriched in the faster diffusing component is collected from the second side of the membrane while the feed is in contact with the membrane. It will be appreciated that the introduction and interruption of the feed, as described, can be continuously cycled to produce any desired amount of permeate. Alternatively, the process can be run as a batch process, i.e., only one feed introduction/interruption cycle.

In a continuous process, the multi-component feed is introduced to the first side of a permeable membrane and intermittently interrupted at selected time intervals such that the entire feed mixture never reaches steady state permeation of the membrane. An enriched permeate stream is collected from the second side of the membrane during the time intervals when the feed is in contact with the membrane. Thus, virtually any desired amount of permeate can be collected. Where a batch process is employed, the introduction of the multi-component feed is discontinued after the predetermined time period has elapsed and an enriched permeate stream is collected. This type of process is suitable in certain chemical analysis contexts where a relatively small permeate sample is all that is required.

Both the continuous and batch embodiments of the process of the present invention are suited to exploit the sorption and/or desorption portions of the permeation response profile for the feed mixture. That is, the permeate can be collected during sorption to obtain a mixture enriched in the faster diffusing compound or compounds or the permeate can be collected during desorption to obtain a mixture enriched in the slower diffusing compound or compounds.

Intermittent interruption of the feed stream is accomplished in one of several preferred manners. In one embodiment, an inert gas is introduced into the feed stream at selected time intervals to interrupt and "segment" the feed into discrete amounts so as to control and maintain the residence time of each "segment" of feed in contact with the membrane to the preselected time, which time is less than that required for the second membrane-permeable component to reach steady-state permeation. In another preferred embodiment, the feed stream is interrupted intermittently and "segmented" by the introduction of an inert liquid at selected time intervals so as to control and maintain the residence time of each "segment" or feed in contact with the membrane to the preselected time, as stated above. In an additional preferred embodiment, the feed is intermittently interrupted and "segmented" physically by a solid barrier or surface, such as a piston, which alternately covers and uncovers the first surface of the membrane, to control and maintain the residence time of each "segment" of feed with respect to the membrane. In another preferred embodiment, the feed stream flow to the membrane is discontinued and the membrane is evacuated with a vacuum for a preselected time, and thereafter the feed is reintroduced to the membrane and the process is repeated. Thus, by employing any one of the above-described means for periodically interrupting and segmenting the feed mixture and choosing the appropriate time interval for the feed to be in contact with the membrane, the permeation process continuously cycles through the sorption-desorption scheme and a permeate enriched in a faster diffusing compound is collected.

One preferred embodiment of the apparatus for carrying out the above-described process comprises a membrane that is permeable to at least two components of a multi-component fluid system in which the two components have differing rates of attainment of steady state permeation through the membrane. The membrane has first and second sides. The apparatus further comprises means for introducing a feed stream of the multi-component fluid system to the first side of the membrane; means for intermittently interrupting the introduction of the feed at preselected time intervals such that one component approaches steady state permeation of the membrane more rapidly than other components prior to each interruption of the feed; and means for collecting permeate enriched in one membrane-permeable component from the second side of the membrane. The feed interrupting means may comprise a valving mechanism which is operated to intermittently interrupt the feed, or a cylinder and piston combination in which the piston is repositionable to alternatingly cover and uncover the first side of the membrane, and thereby "segment" the feed.

DETAILED DESCRIPTION OF THE INVENTION

The present invention includes a method and the associated apparatus for separating membrane-permeable components from one another. The present invention is applicable to large scale use in the chemical process industry, to chemical analysis systems and to many other situations. In its various embodiments, the process of the present invention can be used to purify a feed stream which contains an undesirable component that is membrane permeable or to produce a permeate that is enriched in either a faster or slower diffusing component or components, as desired. The membrane of the present invention must be a semi-permeable membrane having two sides; such as a tubular type membrane of non-porous silicone rubber having one side exposed to the bore of the membrane and the other side being the outside of the tubular membrane; and such as a sheet type membrane of Nafion brand ion-exchanger from DuPont having a side on each surface of the sheet.

Figure 1:
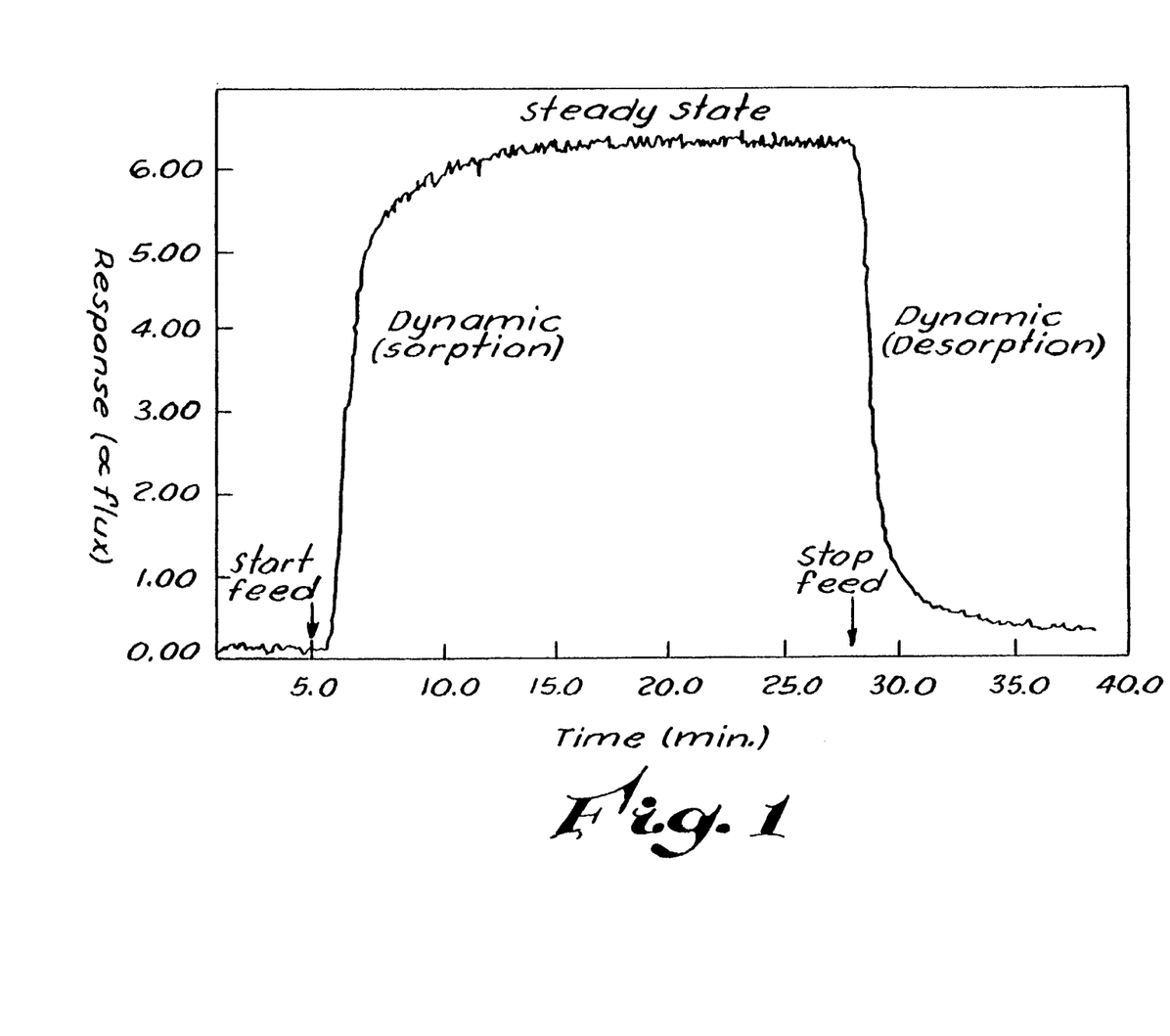
FIG. 1 shows a typical permeation response profile for a membrane-permeable compound.

FIG. 1 shows a typical permeation response profile for a membrane-permeable compound with the regions of permeation labeled sorption, steady-state and desorption. As is depicted in FIG. 1, permeation of a membrane-permeable compound through a membrane Increases from a baseline value to steady-state during an initial time period after the feed is introduced to the permeable membrane. This is sorption. Sorption represents a period of dynamic permeation since the rate of permeation is not constant with time. Similarly, the desorption section of the response profile shows the permeation decreasing or falling off from its steady-state value to a baseline value after introduction of feed to the membrane has been stopped. This period of desorption also represents a period of dynamic permeation.

Figure 2:
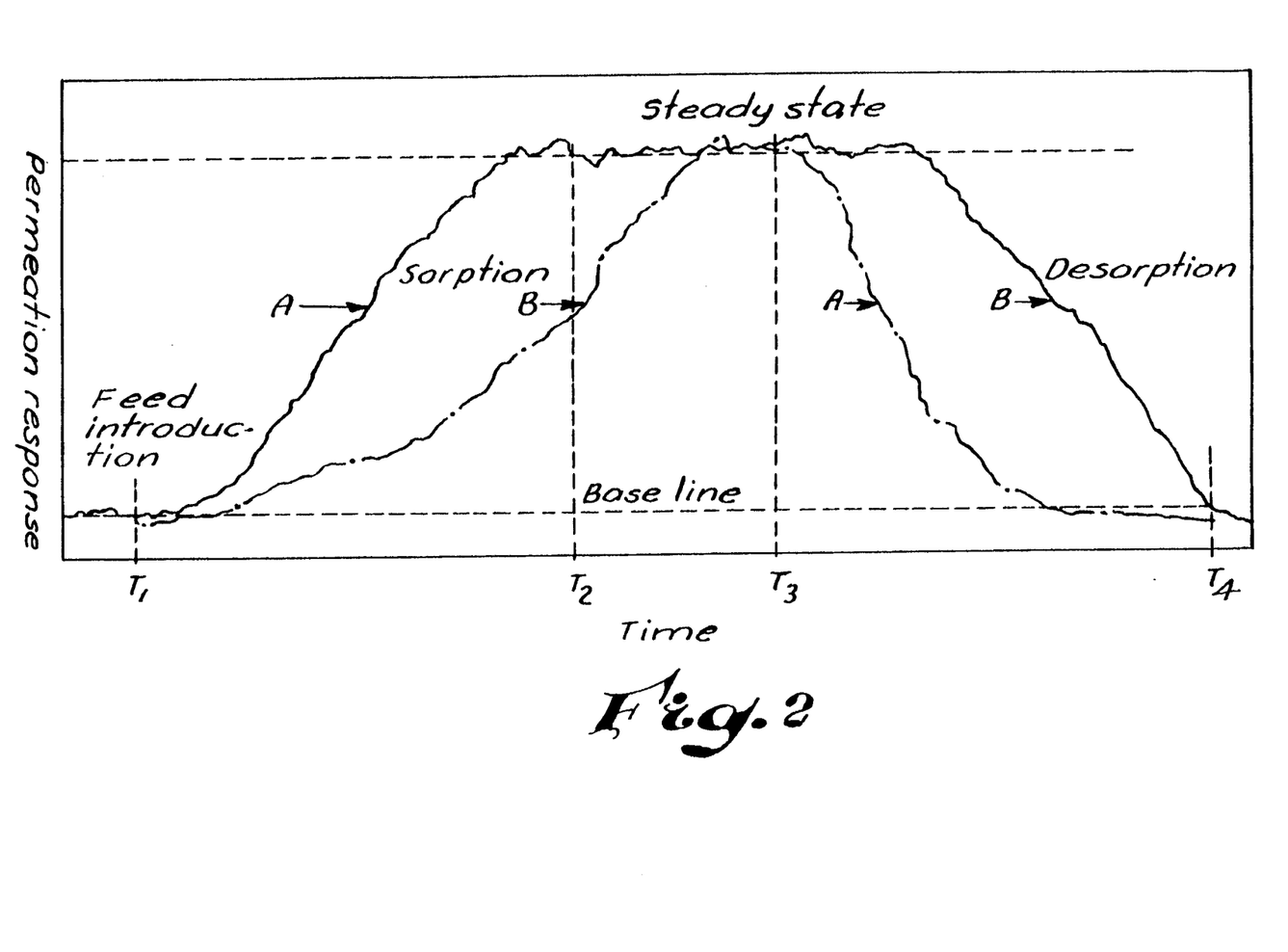
FIG. 2 shows a typical permeation response profile for a two-component mixture.

FIG. 2 shows a typical permeation response profile for a two component mixture consisting of component A and component B, both of which are membrane permeable. As shown component A has a faster rate of attainment of steady-state permeation than does component B and component A has a faster rate of fall-off from steady state permeation than does component B. The process of the present invention is based on the exploitation of these rate differentials.

In one embodiment, the process of the present invention exploits the differential in the rates of attainment of steady-state permeation (sorption) of membrane permeable components by continuously cycling through a feed introduction/feed interruption regime. That is, a multi-component fluid mixture having at least two membrane-permeable components is fed to a first side of a permeable membrane and has a preselected residence time in contact therewith which is of sufficient duration that the compound(s) having a faster rate of attainment of steady-state permeation approach or reach steady-state and the compound(s) having a slower rate of attainment of steady-state permeation do not reach steady-state permeation of the membrane.

With reference to FIG. 2, for example, the feed is introduced to the membrane at a time ($T_1$) and the feed is interrupted at a time ($T_3$), with the time period ($T_3$-$T_1$) being the preselected time period in which the feed mixture is in contact with the membrane. After the predetermined time period has elapsed, and the introduction of the feed to the membrane has been interrupted, the membrane is purged of the feed mixture. During the time period ($T_2$-$T_1$), permeate selectively enriched in component A is collected from the second side of the permeable membrane. The exact value of $T_2$ depends on the specific application and generally is set between $T_1$ and the attainment of steady state. In some applications it will be desirable to begin to collect the permeate some time after $T_1$. Once the membrane has been purged after $T_4$, the feed mixture is again introduced to the membrane and the cycle is repeated.

In another embodiment, the process of the present invention exploits the differential in the rates of fall-off from steady-state permeation to the base line value (desorption) of membrane permeable components. In this embodiment, the permeate stream is enriched in she slower diffusing compound(s), i.e., the compound(s) with the slower rate of fall-off from steady-state permeation. For example, with reference to FIG. 2, the permeate collected during the time interval ($T_4$-$T_3$) will be enriched in component S. Thus, depending on which is the desired component, A or B, the permeate is collected during the appropriate time interval—($T_2$-$T_1$) for component A and ($T_4$-$T_3$) for component B. The exact value of $T_3$ depends on the specific application and generally is set between the attainment of steady state and $T_4$.

Figure 3A:
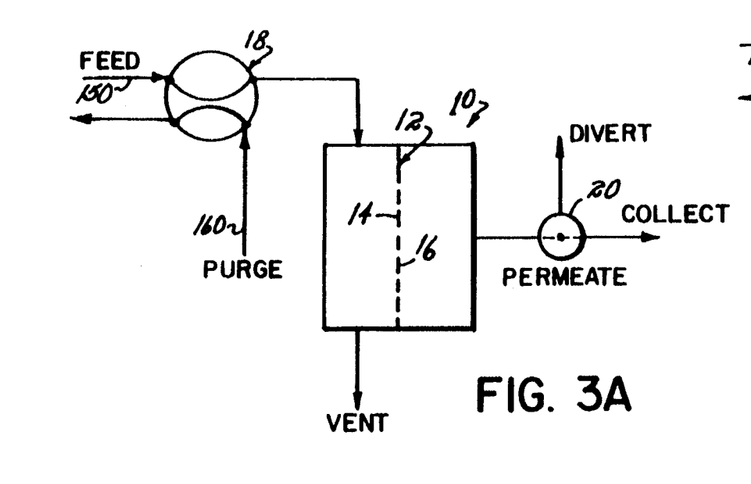
FIG. 3A is a schematic of one embodiment of the apparatus of the present invention.
Figure 3B:
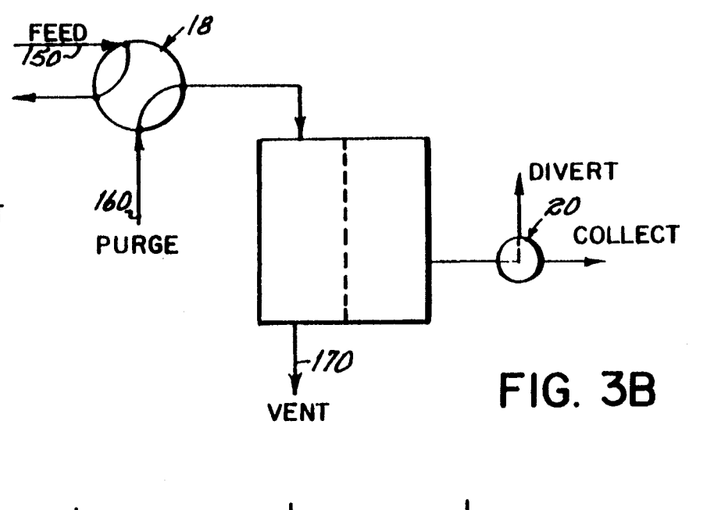
FIG. 3B is a schematic of the apparatus of FIG. 3A in an alternative operative condition.

FIGS. 3A and 3B depict one embodiment of a single-module dynamic permeation membrane apparatus which is used to carry out the process of this invention. The apparatus comprises a membrane module 10 (FIG. 3A) having a permeable membrane 12 positioned therein. A feed stream 150 of a multi-component fluid mixture having at least two membrane permeable components therein, where a first membrane permeable component has a faster rate of attainment of steady-state permeation and a faster rate of fall-off from steady-state permeation than does a second membrane permeable component, analogous to the A–B mixture represented in FIG. 2, is introduced through switching waive 18 to a first side 14 of membrane 12. The enriched permeate stream is collected from a second side 16 of permeable membrane 12 through divert valve 20 while the feed stream is in contact with membrane 12.

After a predetermined time period has elapsed, which time period is preferably less than that required for the second membrane-permeable component to reach steady-state permeation of membrane 12, for example time period ($T_2$-$T_1$) shown in FIG. 2, switching valve 18 is repositioned (FIG. 3B) so that introduction of the feed stream 150 to membrane module 10 is interrupted. A purge stream 160 is introduced to membrane module 10 to purge the module and return the membrane to its prefeed introduction state. When switching valve 18 is switched to introduce the purge stream to membrane module 10, divert valve 20 is switched (FIG. 3B) so that the fluid from the second side 16 of membrane 12 is diverted, and not collected. The purge stream 160 is preferably an inert liquid or gas. Alternatively, once the feed is interrupted, module 10 may be purged by evacuating any residual fluid with a vacuum pump (not shown).

In addition, membrane module 10 may have a vent 170, shown in FIG. 3B, so that during the purging operation, any fluid which does not permeate the membrane 12 is vented from the module prior to switching of switching valve 18 and reintroduction of the feed stream to membrane module 10.

Figure 4:
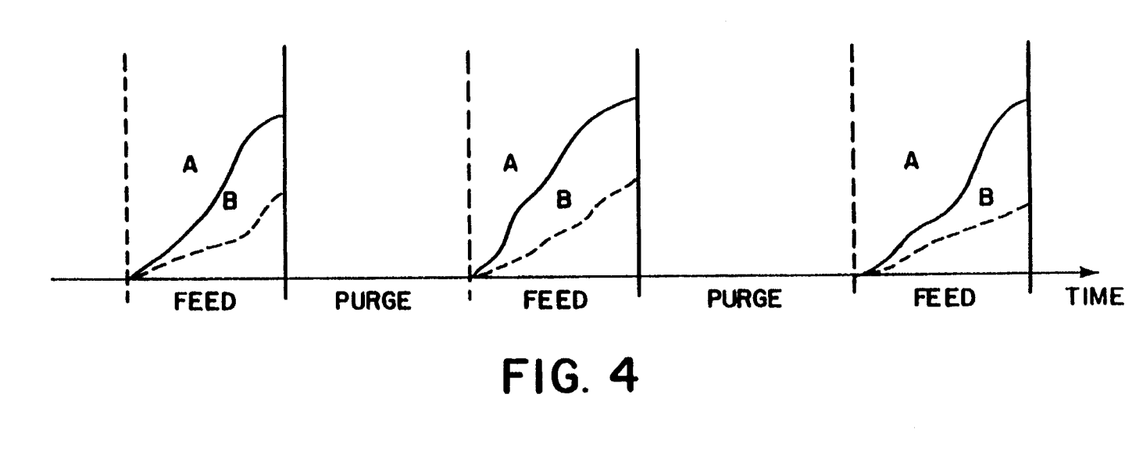
FIG. 4 shows a typical permeate collect profile representative of one embodiment of the process of the present invention.

Continuous cycling of a feed mixture and a purge stream produces a permeate collect profile which is depicted in FIG. 4. The profile shows a repeating sorption section of a permeation curve for a permeate having two components, A and B, wherein the vertical solid lines represent the point in time when switching valve 18 is switched to discontinue introduction of the feed to membrane module 10 and begin introduction of the purge stream to membrane module 10. The vertical dotted lines represent the point in time when switching valve 18 is returned to its original position to begin the introduction of the feed stream and discontinue the introduction of the purge stream. The continuous cycle represented in FIG. 4 produces a sorption permeate enriched in component A relative component B. When switching valve 18 is in position to introduce feed to module 10, divert valve 20 is in position to collect the permeate enriched in component A, and when switching valve 18 is in position to introduce the purge stream to module 10, divert valve 20 is in position to divert the resulting permeate fluid.

The desorption permeate may be collected using the single-module device depicted in FIGS. 3A and 3B by simply reversing the divert valve sequence. That is, while the feed is being introduced to module 10 through switching valve 18, divert valve 20 is in the divert position. Switching valve 18 is then repositioned to a feed interrupt position (not shown) and divert valve 20 is set in the collect position to collect the desorption permeate enriched in component B. Thereafter, switching valve 18 is positioned to introduce the purge stream to membrane module 10 and divert valve 20 is reset to the divert position.

In either embodiment, collecting the sorption or desorption permeate, divert valve 20 may be used to regulate the point in time when collection of the permeate begins and ends. Thus, with reference to FIG. 2, it will be appreciated that the time period when collection of the permeate occurs can be adjusted to collect a permeate with optimum enrichment of the desired component(s).

An alternate desorption technique that has some advantages is to desorb from the first side of the membrane. Referring to FIG. 3B, the purge fluid 160 can be used to remove the feed mixture from the first side of the membrane and then the desorption products from the first side of the membrane can De collected via the vent 170. It is often preferable, in this alternative, to physically cover the other side of the membrane or expose it to a fluid that similarly blocks the membrane surface. However, the desorption products can be collected through both the valve 20 and the vent 170. One advantage of desorbing from the first side of the membrane is that the concentration gradient of a component of the feed mixture is highest on the first side of the membrane.

Figure 5:
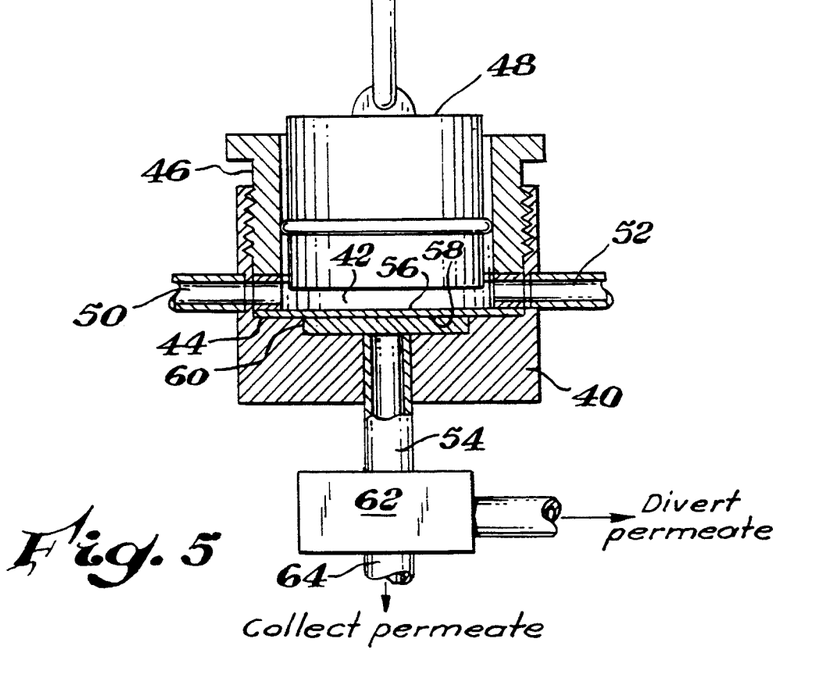
FIG. 5 is a cross-section of one embodiment of the apparatus of the present invention.

An alternative embodiment of the apparatus of the present invention is shown in FIG. 5. The apparatus includes a block 40 having a cavity 42 therein for receiving a permeable membrane 44, cylinder 46, and a piston 48. Cavity 42 communicates with the exterior of block 40 through first channel 50, second channel 52 and third channel 54. Membrane which is permeable to at least first and second components of a multi-component fluid mixture feed, is positioned in cavity 42 such that its first side 56 is exposed to piston 48 and is in communication with first and second channels, 50 and 52, respectively. The second side 58 of membrane 44 is in communication with third channel 54, separating it from channels 50, 52. Membrane 44 may be separated from channel 54 by a porous fruit 60 which supports membrane 44 to prevent it from being damaged or distorted by the flow of feed or the action of piston 48.

A multi-component fluid mixture feed having at least first and second membrane permeable components is introduced to first side 56 of membrane 44 through first channel 50. After the preselected time period has elapsed, which time period is preferably less than that required for a second membrane-permeable component to reach steady-state permeation of membrane 44, piston 48 is actuated in a downward motion to cover first side 56 of membrane 44 and thereby interrupt the introduction of feed to membrane 44. The apparatus additionally includes valve member 62 which can be switched from a first position, wherein the permeate from the second side 58 of membrane 44 is collected, to a divert or discard position wherein the fluid permeating membrane 44 is diverted away from the primary collection line 64. This diverted fluid may be recycled to the membrane separation apparatus or transported by suitable means to a second stage separation module (not shown). By alternatingly covering and uncovering membrane 44 with piston 48, the cyclic dynamic permeation process of this invention is achieved.

the use of the apparatus shown in FIG. 5, the feed may be continuously introduced through channel 50, with piston 48 and cylinder 46 dimensioned such that when piston 48 is in the down position the feed passes around piston 48 and out of block 40 through channel 52. Alternatively, a preselected amount of feed may be introduced into block 40 in a batch-wise manner and piston 48 alternatingly raised and lowered to cover and uncover membrane 44 to act on the batch feed. In either case, and especially when the feed is a gas, channel 52 may be operably connected to a vacuum pump (not shown).

The dynamic membrane permeation apparatus shown in FIG. 5 was evaluated for its ability to exploit the dynamic permeation characteristics of a two-component mixture. A feed mixture of chloroform and acetone, both of which are membrane permeable, was used to evaluate the device.

Figure 6:
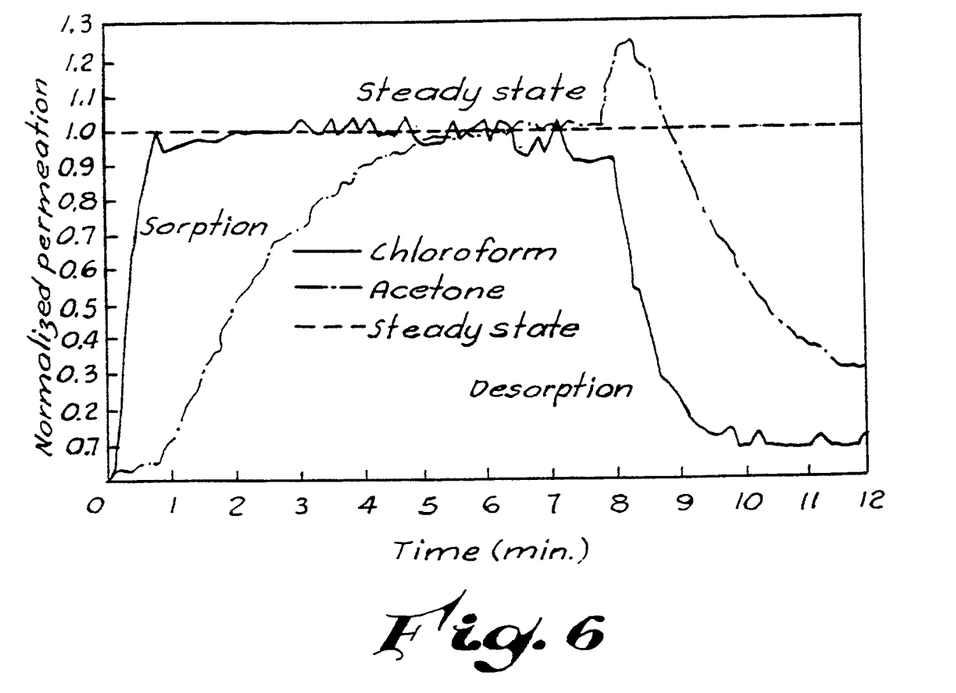
FIG. 6 shows the normalized permeation response curve for a chloroform-acetone mixture.

FIG. 6 shows the permeation data collected for the dynamic separation of chloroform and acetone using the device of FIG. 5. Acetone, being the slower diffusing compound, has a slower rate of attainment of steady-state permeation than does chloroform. Thus, in the sorption segment of the permeation profile, chloroform is significantly enriched in the permeate relative its enrichment during steady-state permeation. During the desorption segment of the permeation profile, acetone is enriched over chloroform relative steady-state enrichment due to the fact that acetone has a slower rate of fall-off from steady-state permeation.

Figure 7:
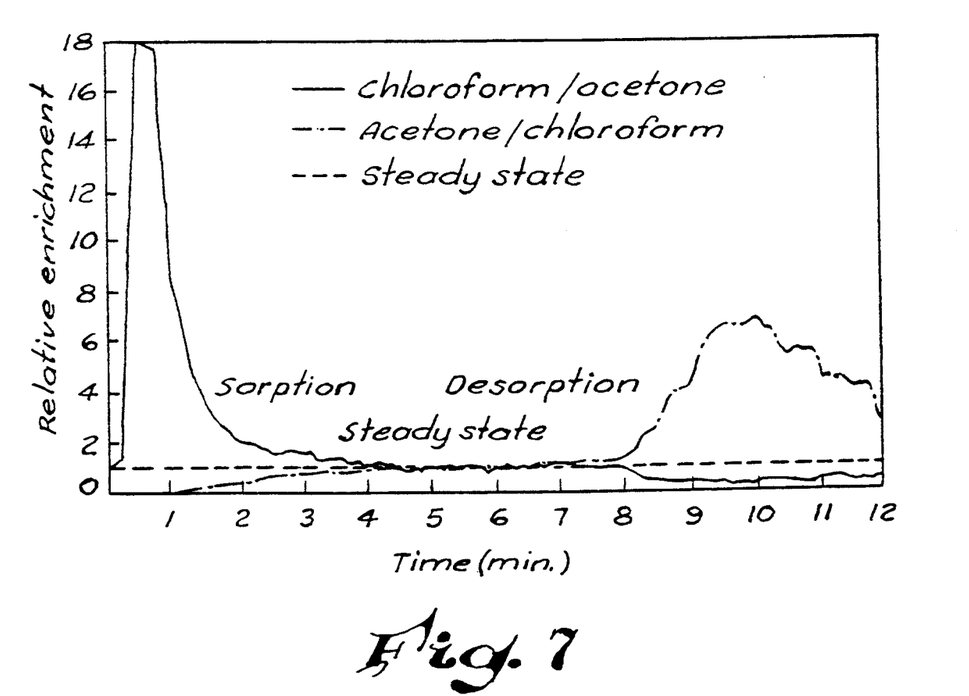
FIG. 7 shows the relative enrichment curve for the chloroform-acetone mixture corresponding to FIG. 6.

The relative enrichment of acetone and chloroform is shown in FIG. 7. This curve is normalized so that enrichment at steady-state permeation is represented by the dotted line at a ratio of 1:1. Thus, as can be seen in FIG. 7, the permeate is significantly enriched in chloroform during the sorption segment of the permeation cycle and the permeate is enriched in acetone during the desorption segment of the permeation cycle. Therefore, with appropriate valving, a permeate stream enriched in the desired component is collected. That is, with reference to the chloroform-acetone example, the permeate collected during sorption is enriched in chloroform and the permeate collected during desorption is enriched in acetone.

It will be appreciated that in certain applications, e.g., purification processes, the permeate is enriched in a component that is undesirable in the feed mixture. In those instances, the enriched permeate collected from the second side of a permeable membrane is discarded and the component remaining in the membrane (depleted or purified of the undesirable component) is collected.

The process of the present invention is particularly beneficial and useful for producing a permeate for chemical analysis using mass spectrometry. The reason for this is that the dynamic permeation separation process produces a permeate which is selectively enriched in one membrane-permeable component vis-a-vis another membrane-permeable component from a multicomponent feed mixture, and thereby serves to reduce the interference signal when the permeate is analyzed. For mass spectrometric applications, it is desirable to interface the apparatus for introducing the enriched permeate directly to the mass spectrometer.

One available apparatus for performing this function is disclosed in co-pending application Ser. No. 455,472, filed on Dec. 22, 1989 in the names of the inventors Mark A. LaPack and James C. Tour entitled "Valve Membrane Combination" now U.S. Pat. No. 5,019,139.

Due to its selectivity and sensitivity, mass spectrometry is a very useful chemical analysis tool for studying membrane separation processes. The results of the dynamic membrane permeation separation process of the present invention were studied using a Balzers QMG 511 quadrupole mass spectrometer (MS) with a 1 to 1023 Dalton mass range. The MS was controlled and data acquired with a PDP 11/23 based computer. The instrumental conditions were as follows:

| | |
|---|---|
| Ionization: electron impact | 1200 v over 15–100 Dalton range |
| Electron multiplier voltage: | 1800 V over 56–120 |

| | -continued |
|---|---|
| | Dalton range |
| Electrometer: | $10^{-7}$ A |
| Filter: | 1 ms |
| Dwell time: | 10 ms |
| Scan rate: | 1 scan/second |

Figure 8:
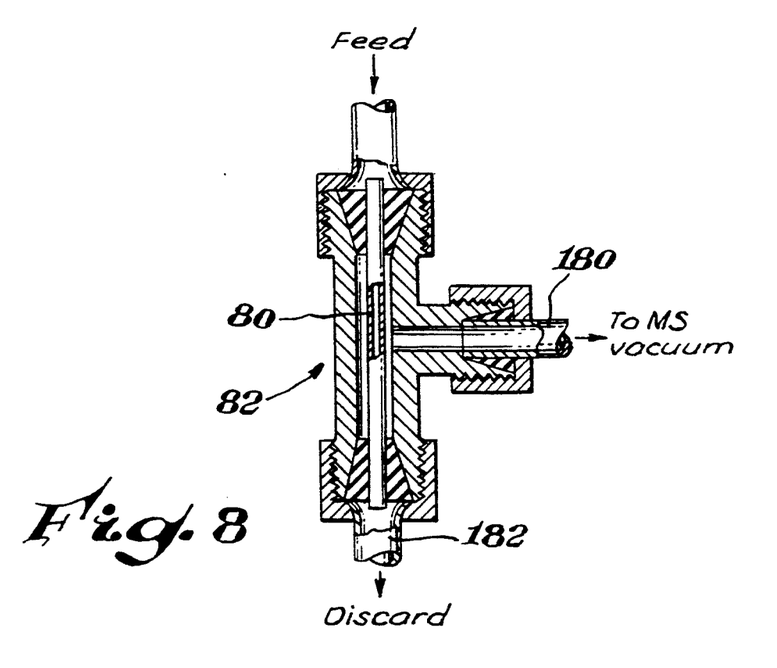
FIG. 8 is a cross-section of a compression sealed flow-through membrane device.

In this particular analysis, the membranes were interfaced with the MS with the compression sealed flow-through membrane device shown in FIG. 8. In the device shown in FIG. 8, a short section of stainless steel tubing, not shown, is inserted at the inlet and the outlet ends of the membrane to facilitate the compression sealing. The compression sealing details of this device are disclosed in the above referenced co-pending application Ser. No. 455,472 filed Dec. 22, 1989 now U.S. Pat. No. 5,019,139 (see FIG. 5 thereof), the specification of which is hereby incorporated herein by reference. The specific membrane used in the present invention is not critical and generally includes a selectively permeable membrane as described in the co-pending application mentioned in this paragraph. A preferred membrane material is silicone rubber. The membranes selected for this study were Silastic cross-linked silicon hollow fibers from Dow Corning. (Silastic is a trademark of Dow Corning.) This membrane material is highly permeable to non-polar volatile organics, yet exhibits poor permeability for air and water feed matrices. One inch long fibers were used in all cases. Permeations from gas feeds were studied using a 0.32 mm I.D. ×0.65 mm O.D. hollow fiber and permeations from water feeds were studied using a 0.5 mm I.D. ×0.94 mm O.D. hollow fiber.

In operation, the feed was pumped through the inside or hollow fiber 80, which is positioned membrane module 82. The outside of hollow fiber membrane 80 was exposed to the MS vacuum, not shown, via permeate outlet tube 180. The fluid not permeating fiber 70 was discarded through discard cutlet tube 182. Appropriate valving, not shown, may be employed where the device shown in FIG. 8 is used in a continuous, cyclic operation to control the collection and diversion of the permeate. In the present example, however, the device was operated and results analyzed based on a once-through or batch operation. The enriched permeate was therefore fed directly to the MS for analysis. Gas feeds were pumped through the membrane device at a rate of 100 cc/min. With a suitable air pump and water feeds were pumped through the membrane at a rate of 10 cc/min. With a suitable fluid pump. The temperature of the membrane was held constant at 30° C.

The following reagents were used:

Acetone

Butane

Ethyl Benzene

Methylene Chloride

Toluene

Gas feed mixtures were prepared by injecting aliquots of each organic into a 100 l Saran bag filled with nitrogen. The liquid feed was 3 ppm (mole/mole) methylene chloride in deionized water.

Figure 9A:
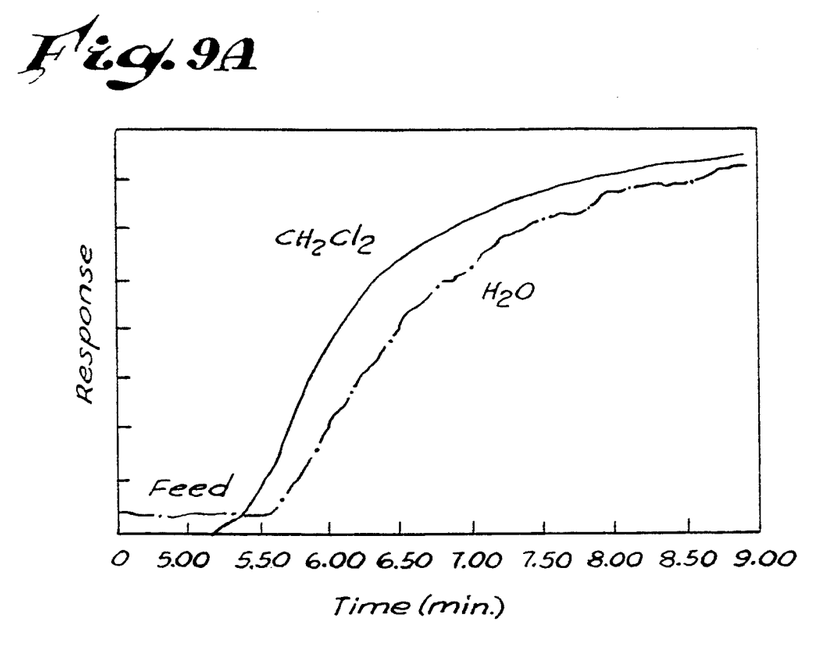
FIG. 9A shows the normalized permeation response curve for a methylene chloride-water mixture.
Figure 9B:
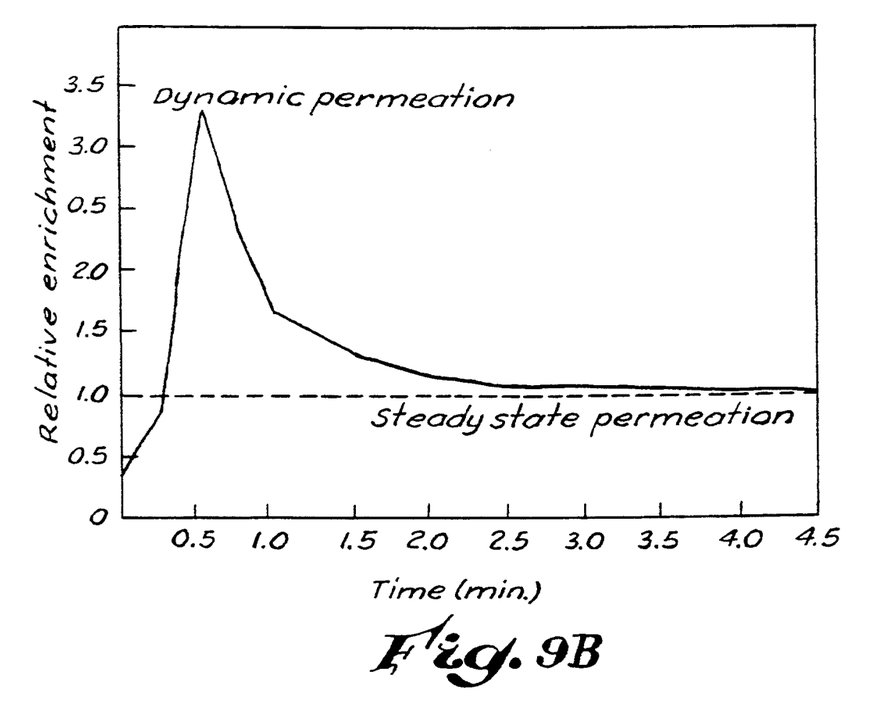
FIG. 9B shows the relative enrichment curve for the methylene chloride-water mixture corresponding to FIG. 9A.

FIG. 9A shows normalized mass spectrometric data which illustrates the change in the efficiency for the silicon membrane separation of methylene chloride from water as the system approaches steady-state permeation. Methylene chloride diffuses through the membrane faster and therefore reaches steady-state permeation before the water does, resulting in a peak enrichment, shown in FIG. 9B, of about 3.5 times that of the steady-state enrichment.

The process of the present invention was also applied and tested in the context of separating interferents in an analytical setting. More particularly, using the apparatus of FIG. 8, three different feed mixtures were analyzed for their permeation response profile. The first feed mixture consisted of 10 cc of butane in 100L of nitrogen. The second feed mixture consisted of 40 ml of acetone in 100L of nitrogen. The third mixture was a combination of the first two mixtures. Since the silicon hollow fiber membrane employed is highly permeable to non-polar organic solvents and exhibits poor permeability for air and water feed matrices, the resulting permeation data for the butane and acetone mixtures is not dependent upon or affected by the presence of the nitrogen, which ostensibly was largely rejected by the membrane.

Figure 10A:
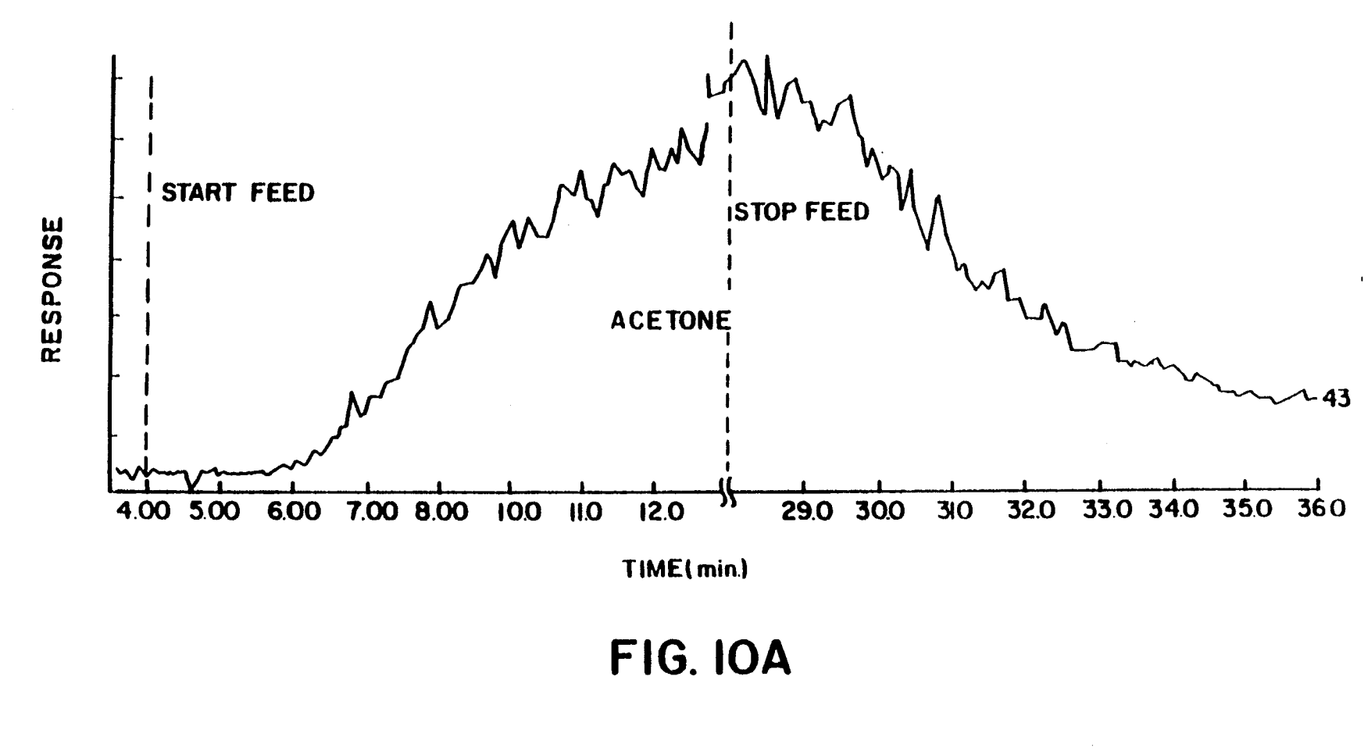
FIG. 10A shows the permeation response curve for acetone in nitrogen.
Figure 10B:
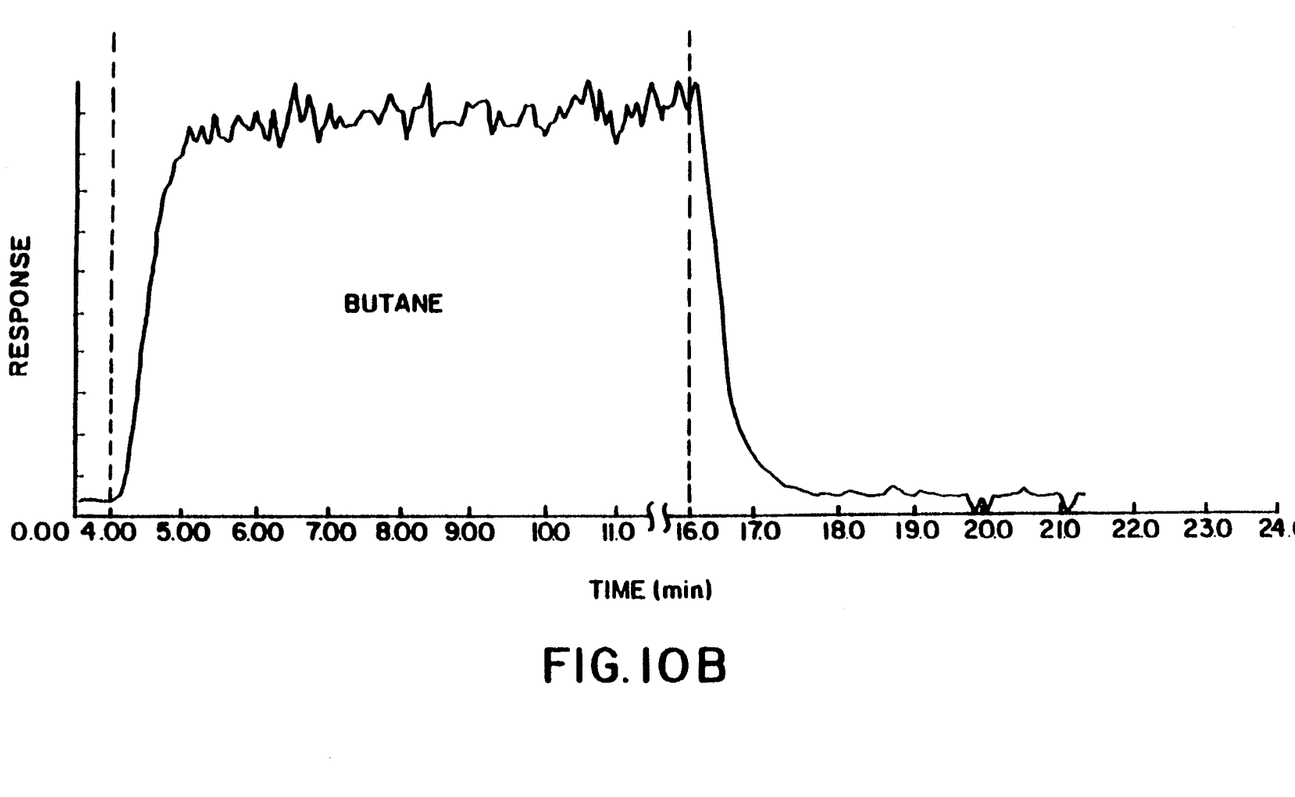
FIG. 10B shows the permeation response curve for butane in nitrogen.

FIG. 10A shows the permeation response curve for the acetone-nitrogen mixture and FIG. 10B shows the permeation response curve for butane in the butane-nitrogen mixture. Comparison of FIGS. 10A and 10B reveals that butane has a faster rate of attainment of and fall-off from steady-state permeation than acetone.

Figure 11A:
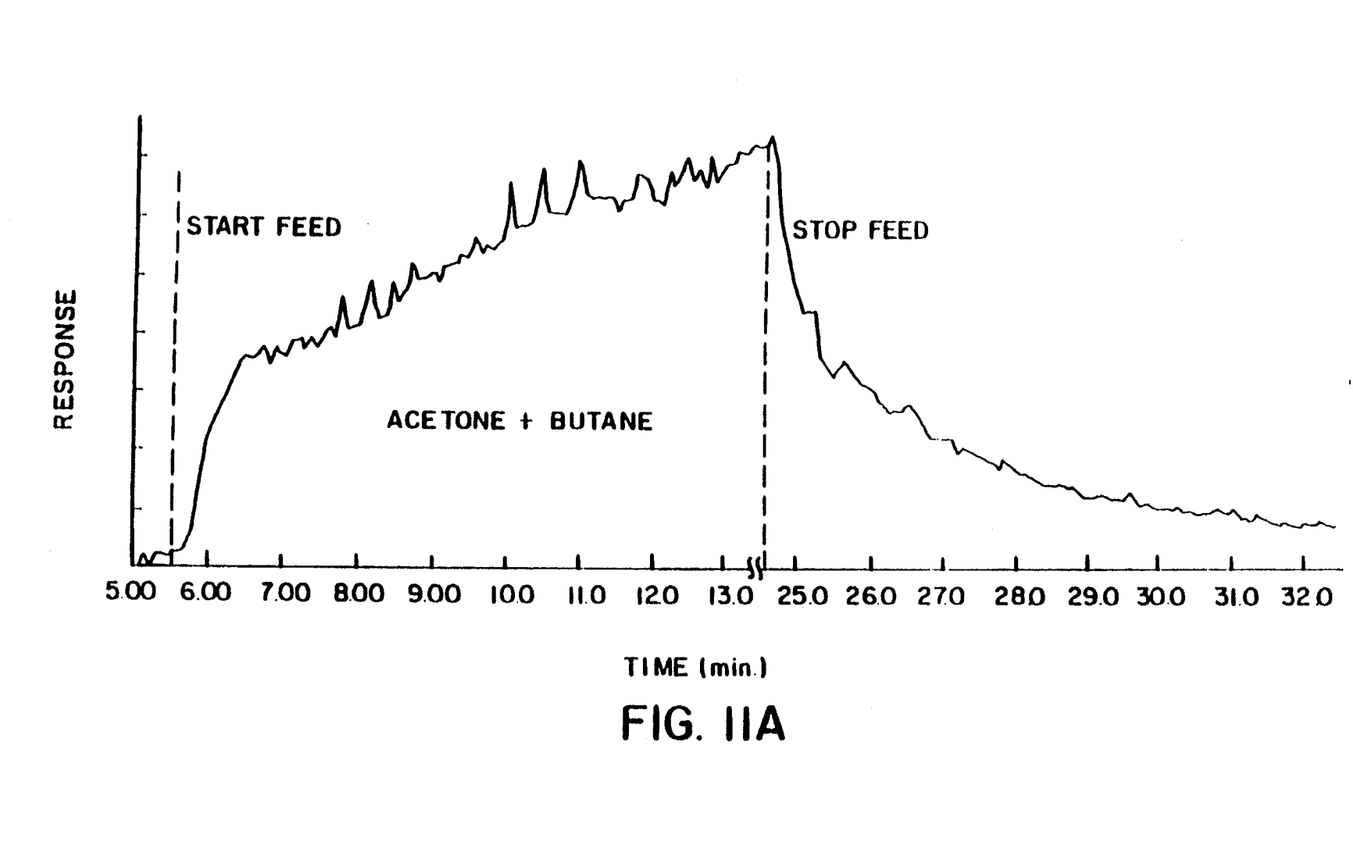
FIG. 11A shows the permeation response curve for an acetone-butane mixture in nitrogen.
Figure 11B:
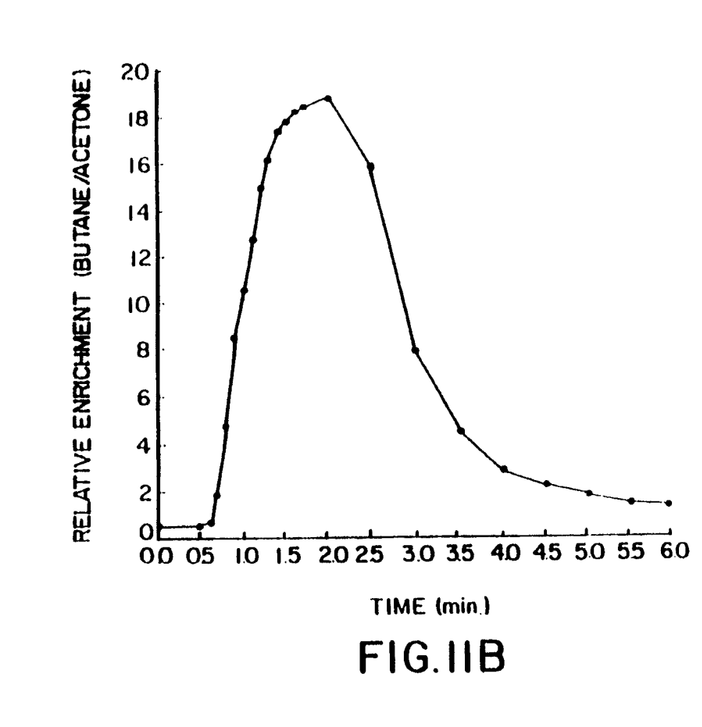
FIG. 11B shows the relative enrichment of butane over acetone during sorption.
Figure 11C:
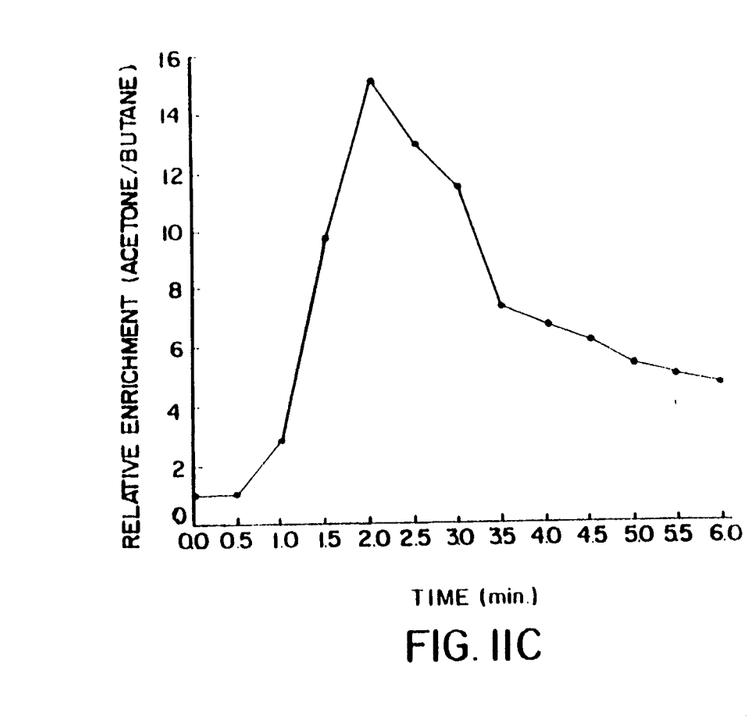
FIG. 11C shows the relative enrichment of acetone over butane during desorption.

FIG. 11A shows the permeation response curve for the acetone-butane mixture in nitrogen. This figure, which is the addition of the permeation response curves shown in FIGS. 10A and 10B, represents the permeation of both acetone and butane. FIG. 11B shows the relative enrichment of butane over acetone during sorption and FIG. 11C shows the relative enrichment of acetone over butane during desorption. Both curves shown in FIGS. 11B and 11C are normalized to steady-state permeation conditions. Thus, the faster diffusing component, butane, was enriched over acetone during sorption, and the slower diffusing component, acetone, was enriched over butane during desorption.

When studying FIGS. 11B and 11C, it will be appreciated that when the highest purity of permeate is desired, then the time of collection will be relatively short, e.g., in FIG. 11B collection could be from 1.6 to 2.5 min. and in FIG. 11C collection could be from 1.75 to 2.5 min. Conversely, when the highest amount of permeate is desired, then the collection time will be longer, e.g., in FIG. 11B the time of collection could be from 0 to 4 min. and in FIG. 11C collection could be from 0 to 6 min.

The process of the instant invention can also include the step of heating and/or cooling the membrane. Heating the membrane will, for example, generally reduce the time needed to desorb the second component from the membrane and decrease the time needed to attain steady-state. In addition, the selectivity of a membrane can change when it is heated or cooled.

The process of the instant invention can use a semi-permeable membrane comprising a bulk phase and a filler phase of different composition than the bulk phase. The use of the filler phase can enhance the difference between the rate at which a first component approaches steady-state permeation of the membrane relative to the rate at which a second component approaches steady-state permeation of the membrane and/or the rate at which a first component desorbs from the membrane relative to the rate at which a second component desorbs from the membrane. In addition, the use of the filler phase can enhance the amount of a component absorbed by the membrane.

The shape of the filler may consist for example of a film, rods, fibers, beads, or other particle shapes. The filler can be porous or non-porous. The material of the filler may consist of for example a polymer such as a latex, a ceramic, silica, alumina, zeolite, a mineral, a metal or carbon. Thus, the precise shape and material of the filer is not critical. However, when a filler is used it is best if it enhances the difference between the rate at which a first component approaches steady-state permeation of the membrane relative to the rate at which a second component approaches steady-state permeation of the membrane or the rate at which a first component desorbs from the membrane relative to the rate at which a second component desorbs from the membrane.

Figure 12:
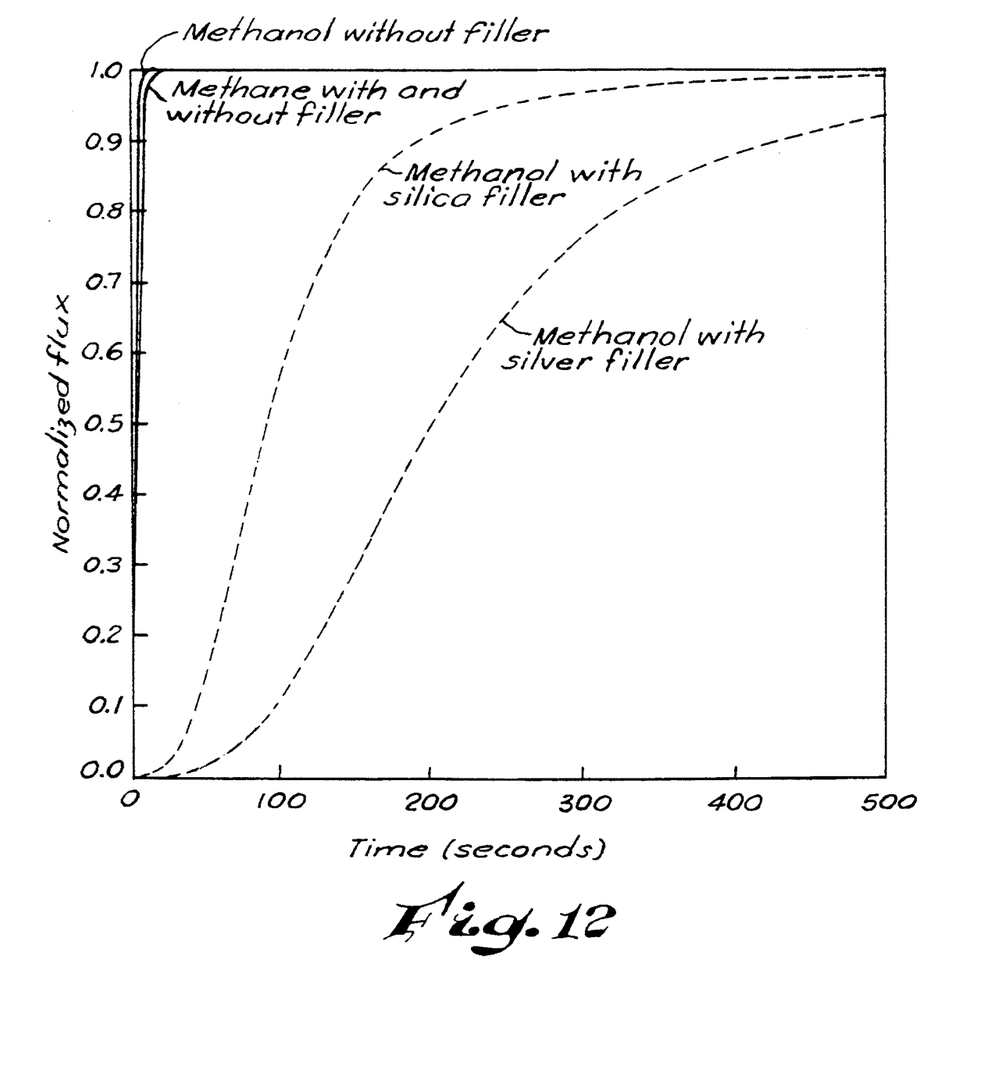
FIG. 12 shows the effect of a composite membrane used in the instant invention.

The use of a filler in the semi-permeable membrane of the instant invention can have a dramatic effect as shown by FIG. 12. Four curves are shown in FIG. 12. One curve shows the rate at which methane approaches steady-state permeation of: (a) a silicone rubber membrane without a filler; or (b) a silicone rubber membrane containing thirty one weight percent silica filler. A second curve shows the rate at which methanol approaches steady-state permeation of a silicone rubber membrane without a filler. It will be noted that there is little difference between this rate and the rate for methane. A third curve shows the rate at which methanol approaches steady-state permeation of a silicone rubber membrane containing thirty one weight percent silica filler. It will be noted that now there is a much greater difference between this rate and the rate for methane. A fourth curve shows the rate at which methanol approaches steady-state permeation of a silicone rubber membrane containing ten weight percent silver filler having a particle size of from about two to about three and one half micrometers. It will be noted that now there is an even greater difference between this rate and the rate for methane despite the fact that the effect of tortuosity has been normalized.

The process of the instant invention can also use a semi-permeable membrane comprising a layer of one material upon a layer of another material, i.e., a composite membrane. One example of this approach is to coat a silicone rubber membrane with a layer of silica particles. Another example is to coat a porous alumina membrane with a layer of polyethylene or silicone rubber.

The above examples, of course, are not intended to exhaust the possible applications of the present invention. For example, the present invention can be coupled with additional separation steps such as chromatography, distillation, this membrane method, other membrane methods, pressure swing absorption, stripping columns, extractors, etc. The present invention has many embodiments as described and claimed herein.

We claim:

1. A membrane separation process in which a non-porous semi-permeable membrane having a first side and a second side is used to separate components in a multi-component fluid feed mixture wherein a first component of said feed mixture approaches steady-state permeation of said membrane at a faster rate than a second component of said mixture, said membrane comprising at least two phases, said process comprising the steps of:

(a) introducing said feed mixture to said first side of said membrane so that said first and second components begin to approach their steady-state permeation of said membrane; and (b) collecting from said second side of said membrane for a predetermined period of time a new mixture enriched in said first component relative to said feed mixture as a function of a difference in dynamic membrane permeability rates of said first and second components, the predetermined period of time beginning before said second component attains steady-state permeation of said membrane.

2. The process of claim 1 further comprising the step of removing said feed mixture from said first side of said membrane.

3. The process of claim 2 further comprising the step of collecting from said second side of said membrane for another predetermined period of time a different mixture enriched in said second component relative to said feed mixture, the another predetermined period of time being after the step of removing said feed mixture from said first side of said membrane.

4. The process of claim 3 wherein the steps are repeatedly cycled to repeatedly produce a mixture selected from the group consisting of said new mixture and said another mixture.

5. The process of claim 2 wherein the step of removing said feed mixture from said first side of said membrane is done with an inert fluid.

6. The process of claim 2 wherein the step of removing said feed mixture from said first side of said membrane is done with a vacuum.

7. The process of claim 2 wherein the step of removing said feed mixture from said first side of said membrane is done by physically covering said first side of said membrane with a material that is essentially impermeable to said first and second components.

8. The process of claim 1 further comprising the step of subjecting said new mixture to chemical analysis.

9. The process of claim 3 further comprising the step of subjecting a mixture to chemical analysis, the mixture selected from the group consisting of said new mixture and said another mixture.

10. The process of claim 2 further comprising the step of collecting from said first side of said membrane for another predetermined period of time a different mixture enriched in said second component relative to said feed mixture, the another predetermined period of time beginning after the step of removing said feed mixture from said first side of said membrane.

11. The process of claim 1 wherein the porous semipermeable membrane comprises two phases consisting essentially of a bulk phase and a filler phase.

12. The process of claim 1 wherein the porous semipermeable membrane comprises two phases consisting essentially of a first layer and a second layer.

13. A membrane separation process in which a nonporous semi-permeable membrane having a first side and a second side is used to separate components in a multi-component fluid feed mixture wherein a first component of said feed mixture approaches steady-state permeation of said membrane at a faster rate than a second component of said mixture, said membrane comprising at least two phases, said process comprising the steps of:

(a) introducing said feed mixture to said first side of said membrane so that said first and second components begin to approach their steady-state permeation of said membrane;

(b) removing said feed mixture from said first side of said membrane; and (c) collecting from said second side of said membrane for a predetermined period of time a new mixture enriched in said second component relative to said feed mixture as a function of a difference in dynamic membrane permeability rates of said first and second components, the predetermined period of time beginning after step (b).

14. The process of claim 13 wherein the porous semipermeable membrane comprises two phases consisting essentially of a bulk phase and a filler phase.

15. The process of claim 13 wherein the porous semipermeable membrane comprises two phases consisting essentially of a first layer and a second layer.

16. A method of purifying a multi-component fluid system by selectively separating one component from the multi-component fluid system, which has at least two membrane-permeable components, using a nonporous semi-permeable membrane having a first side and a second side, a first of the membrane-permeable components having a rate of attainment of steady-state permeation through a membrane greater than that of a second of the membrane-permeable components, said membrane comprising at least two phases, said process comprising the steps of:

introducing a selected amount of the multi-component fluid system to said first side of said semi-permeable membrane for a predetermined period of time to separate the first component from the second component thereby purifying said multi-component fluid system; and removing the purified multi-component fluid system from said first side of said semi-permeable membrane.

17. The process of claim 16 wherein the porous semipermeable membrane comprises two phases consisting essentially of a bulk phase and a filler phase.

18. The process of claim 16 wherein the porous semipermeable membrane comprises two phases consisting essentially of a first layer and a second layer.

19. A membrane separation process in which a nonporous semi-permeable membrane having a first side and a second side is used to separate components in a multi-component fluid feed mixture wherein a first component of said feed mixture approaches steady-state permeating of said membrane at a faster rate than a second component of said mixture, said membrane comprising at least two phases, said process comprising the steps of:

(a) introducing said feed mixture to said first side of said membrane so that said first and second components begin to approach their steady-state permeation of said membrane.

(b) removing said feed mixture from said first side of said membrane; and (c) collecting from said first side of said membrane a new mixture having a composition different than said feed mixture.

20. The process of claim 19 wherein the porous semipermeable membrane comprises two phases consisting essentially of a bulk phase and a filler phase.

21. The process of claim 19 wherein the porous semipermeable membrane comprises two phases consisting essentially of a first layer and a second layer.

* * * * *